United States Patent [19]

Vergara

[11] 4,201,201

[45] May 6, 1980

[54] ORTHOPEDIC DEVICE FOR PROPPING AND ALIGNING THE VERTEX END POINT OF A SUNKEN NOSE

[76] Inventor: Ruben L. Vergara, 28-5 Graciela, Col., Guadelupe Tepeyac, Mexico City, 14, Mexico

[21] Appl. No.: 910,004

[22] Filed: May 26, 1978

Related U.S. Application Data

[63] Continuation of Ser. No. 727,218, Sep. 27, 1976, abandoned.

[51] Int. Cl.² ............................................. A61F 5/08
[52] U.S. Cl. .................................. 128/76 C; 128/342
[58] Field of Search .................. 128/76 C, 342, 89 R, 128/83, 87 R

[56] References Cited

U.S. PATENT DOCUMENTS

| | | | |
|---|---|---|---|
| 1,014,758 | 1/1912 | Knowlson | 128/342 |
| 1,597,331 | 8/1926 | Thurston et al. | 128/342 |
| 2,515,756 | 7/1950 | Bove | 128/342 |
| 3,108,588 | 10/1963 | Smith | 128/76 C |
| 3,635,215 | 1/1972 | Shea et al. | 128/130 |

Primary Examiner—Robert W. Michell
Assistant Examiner—Michael H. Thaler
Attorney, Agent, or Firm—Michael J. Striker

[57] ABSTRACT

An orthopedic device in form of an inlay insertable into the nose for propping the nasal vertex and the point of the nose, so as to tauten the nostrils of a weakened inwardly sunken nose the point of which is inadequately supported by the nasal septum bone and its lower central cartilage. The inlay is essentially an elongate flexible body having two abutting terminals and a central intermediate beam-like portion and configured to preclude its sliding within the nose and penetrating into the interior nasal cavity and the nasal fossa and also to prevent it from sliding out of the nose. The inlay is accompanied by a hooked puller enabling its retraction from the nasal cavity. The inlay is preferably manufactured from a plastic material, such as for instance polyethylene that does not tend to cause allergic reactions in the human organism.

12 Claims, 6 Drawing Figures

FIG. 4
FIG. 5
FIG. 6
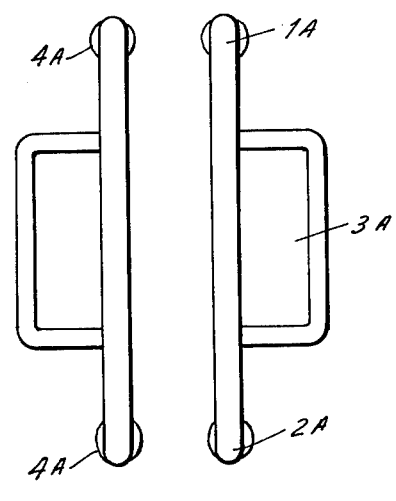
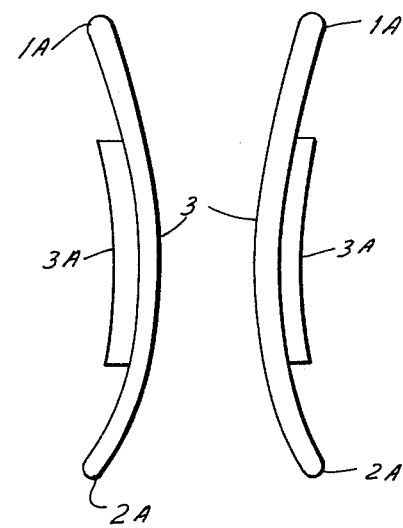
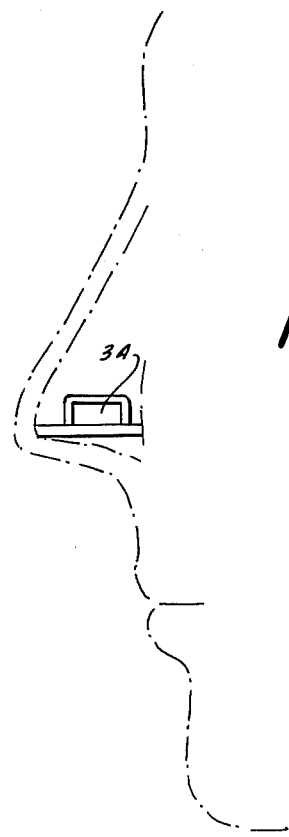

ORTHOPEDIC DEVICE FOR PROPPING AND ALIGNING THE VERTEX END POINT OF A SUNKEN NOSE

This is a continuation, of application Ser. No. 727,218, filed Sept. 27, 1976 now abandoned.

BACKGROUND OF THE INVENTION

Generally stated, the present invention relates to orthopedic nasal devices and more particularly to a propping inlay insertable into the nose for aligning the nasal vertex and lifting the inwardly sunken nose.

It is well known that some persons suffer from a defect resulting from their nose having a tip which curves inwardly into the facial line, thus presenting an unaesthetic appearance.

This defect is caused by a short or damaged septum bone or by an extreme softness of the cartilage which forms a continuation of said bone and supports the lower extremity of the nose in the region of the tip of the nose. If this is the case the nostrils, i.e. the side walls of the nose, being pliable, the nose sinks toward the face bones in its tip region.

Some persons try to have this defect eliminated by surgery. This surgery is usually very expensive and in many cases does not have satisfactory results. Moreover, such plastic surgery ought to be performed by specialized and expert surgeons which in many countries are not yet very numerous.

The invention provides an economical and efficient device that avoids and eliminates the need for costly surgical interventions, a device available to persons wishing to get rid of this inconvenient sunken nose appearance in a practical and simple manner. The orthopedic device according to the present invention may be employed by the persons concerned without requiring any outside assistance.

The maxilla bones of the human skull extend a considerable portion into the region of the nose and form the hard nasal back wall. The human nose has two entrance passages called vertibules which are separated from one another by a bone known as the septum. This septum transgresses in its lower section into a soft certilage extension. Beyond the hard back wall, the nose cavity transits into the so-called nasal fossa extending over the palate.

The orthopedic device of the invention may abut against this hard back wall bounding the nasal cavity.

SUMMARY OF THE INVENTION

It is an object of the present invention to provide a supporting orthopedic nasal inlay available for utilization by any person having an inwardly sunken or curved nose tip.

Another object of the present invention is to provide an economical instrument for propping and making taut the nostrils, for aligning the nose vertex and elevating the nose tip.

A concomitant object of the present invention is to provide such an orthopedic inlay which, when inserted into the nasal cavity, lifts the lower portion and the tip of a nose having a sunken configuration.

Still another object of the present invention is to provide a nasal orthopedic device of the above-described type, which may be easily positioned in the nasal cavity and equally easily retracted therefrom by means of a hooked puller.

In accordance with the above indicated objects and others which will become apparent hereinafter, the device of the present invention comprises, briefly stated, a beam-like body having at each end thereof a rounded enlarged terminal and between these terminals an intermediate flat and thin portion wherein the length of this body mates with the extent of the nostrils in a manner such that, when inserted, it keeps th nostrils taut and elevates the nose tip over the facial region around the nose. The inlay body is provided with an oblong protuberance which is narrowed relative to the intermediate portion and which extends therefrom upwardly to engage the side of the available nasal cartilage or hard septum bone.

In one of the currently preferred embodiments, the intermediate portion is upwardly curved for improving its flexibility.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 4 is a frontal view showing another embodiment of the invention;

FIG. 5 is a side view of the device illustrated in FIG. 4; and

FIG. 6 shows the device of FIG. 4 located in the interior of the nose.

DESCRIPTION OF THE PREFERRED EMBODIMENTS

Figure 1:
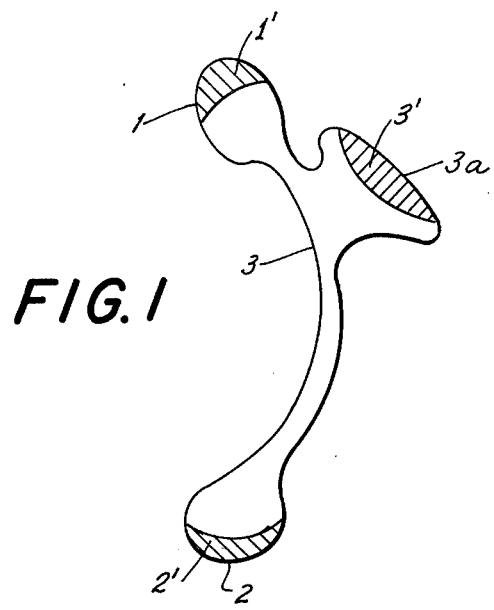
FIG. 1 is a perspective view of the flexible orthopedic device in accordance with the present invention.
Figure 2:
FIG. 2 is a side view of a hooked puller serving for retracting the orthopedic propping device from the nasal cavity.
Figure 3:
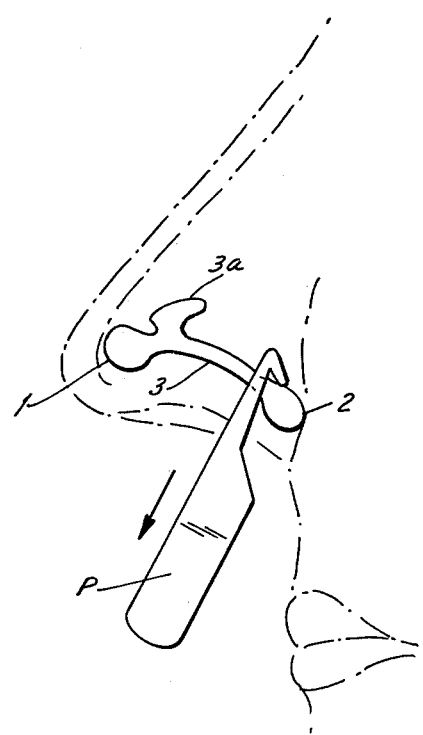
FIG. 3 diagrammatically illustrates the manner in which the device of FIG. 1 is located in the nasal cavity and how the hooked puller is utilized for retracting the device from the nose.

In FIGS. 1 to 3, the orthopedic propping or supporting device of the invention is shown as having two terminals 1 and 2 connected by an intermediate beam-like arched portion 3. This device is mounted by inserting it with the terminal 1 into the nose, terminal 1 being the top section of the device and intended to support the vertex and tip of the nose in such a manner as to lift the same into the desired position. The terminal 2 serves for abutting the orthopedic device in one nasal vestibule against the upper extension of the maxillary bones. A protuberance 3a projects upwardly from the intermediate portion 3; it has an attenuated thickness and is positioned to engage either the septum bone or the cartilage. After the device has been inserted into the nasal vestibule, the intermediate portion 3 keeps the device immobilized inside the nose. The intermediate portion 3 is shaped and dimensioned for preventing any displacement of the device from its desired position.

FIG. 2 shows one possible embodiment of a hooked puller P serving for retracting the device carefully from the nasal cavity.

FIG. 3 displays the device according to the invention after it has been inserted into the nasal vestibule and also shows the hooked puller P in readiness for retracting the device from the nose.

A second embodiment of the orthopedic propping device according to the invention is shown in FIGS. 4 to 6.

Here, FIGS. 4 and 5 illustrate this flexible orthopedic device as having a curved configuration and as being provided with an intermediate portion 3 including a substantially central protuberance 3A in the form of either a planar full plate or a vaulted beam. The intermediate portion 3, 3A ends in two terminals 1A and 2A. The drawings show the side of the device which serves to lift the vertex and the tip of the nose and to give thereto an appealing appearance. The terminal 2A serves as a base for abutting the device against the upper bony extension of the maxillary bones. Surfaces 4A of the terminals 1A and 2A and of the protuberances 3A are specifically coated for smoothly engaging the nasal surfaces which they contact.

FIG. 6 is illustrative of the location of the flexible propping device inside the nose cavity.

It will be understood, of course, that the shape and dimensions of each orthopedic device according to the invention will have to mate with the dimensions inside each individual nose.

Preferably, the entire orthopedic device is made of a synthetic plastic material of the type that does not cause allergic reactions and also does not tend to be rejected by the respective human organism. A preferred material for achieving this, as experiments have evidenced, is polyethylene.

The extremities on which the orthopedic flexible device is to abut the nasal walls, as well as the hooked puller, are perfectly smooth for preventing any scratching effect. They may also be coated with a soft material (see sections 1', 2', and 3' shown in FIG. 1) for avoiding any irritation of the nasal walls or of the nostrils.

For flexibility purposes, it is advantageous to have the intermediate portion 3 most pronouncedly arched adjacent the front terminal of the device.

The orthopedic device of the invention is configurated and thin enough for permitting an unobstructed passage of air and for not causing respiratory difficulties to the person employing the device.

The propping device according to the invention may be manufactured in various colors, such as for instance a neutral color, which blends well with the skin and prevents the device from being detected at a first glance. The color of the device may, however, also be selected to coincide with the skin color of the user. Disguising of the device is aided by its semicircular curved form, enabling it to be concealed from sight within the nasal vestibule.

While the invention is illustrated and described as embodied in FIGS. 1 to 6, it is not intended to be limited to the details shown, since various modifications and structural changes may be made without departing in any way from the spirit of the present invention.

It will be understood that each of the elements described above, or of their portions, or two or more together, may also find a useful application in other types of devices differing from the types described above.

Without further analysis, the foregoing will so fully reveal the gist of the present invention that others can, by applying current knowledge, readily adapt it for various applications without omitting features that, from the standpoint of prior art, fairly constitute essential characteristics of the generic and/or specific aspects of this invention.

What is claimed as new and desired to be protected by Letters Patent is set forth in the appended claims:

1. A device for improving the appearance of a nose, said device comprising two separate propping elements each having an elongated flexible body portion and two terminal portions at the respective ends of said body portion, and each element substantially concealed from view when so accommodated in one nostril of the nose that said flexible body portion urges said terminal portions into contact at the regions of the nasal fossa and of the tip of the nose with the mucous membrane bounding the one nostril to thereby prop the tip region and prevent the undesired shifting of said propping element both into the nasal fossa and out of one nostril, said body portion being provided with a projection having outer surface so shaped as to correspond to and engage the mucous membrane at the region of the septum when said element is accommodated in the one nostril.

2. The device defined in claim 1, and comprising in combination therewith a hooked puller engageable with said device and configured for enabling extraction of the device from the nose.

3. The device defined in claim 1, wherein the material of said propping elements is of a type which does not cause allergic reactions and is not prone to be rejected by the human organism.

4. The device defined in claim 3, wherein said material is polyethylene.

5. The device defined in claim 1, wherein said flexible body portion is of a curved configuration.

6. The device defined in claim 5, wherein said intermediate portion is curved over its entire length.

7. The device defined in claim 1, wherein said portions have smooth and rounded contact surfaces.

8. The device defined in claim 1, wherein said propping elements are of a material having a color tending to prevent detection of the device in the nose at a first glance.

9. The device defined in claim 1, wherein said propping elements are of a material having a color selected to correspond substantially to the skin color of a user.

10. The device defined in claim 1, wherein said terminal portions are rounded.

11. The device defined in claim 1, wherein said terminal portions have at least one transverse dimension exceeding that of said body portion.

12. The device defined in claim 1, wherein said propping elements have a coating of a soft protective material at least on said contact surfaces.

* * * * *